United States Patent
Srayeddin

(10) Patent No.: US 10,245,128 B2
(45) Date of Patent: Apr. 2, 2019

(54) DAMPING DENTAL ROOT POST KEY

(71) Applicants: National Guard Health Affairs, Riyadh (SA); King Saud bin Abdulaziz University for Health Sciences, Riyadh (SA); King Abdullah International Medical Research Center, Riyadh (SA)

(72) Inventor: Bassam Nawaf Srayeddin, Rafha (SA)

(*) Notice: Subject to any disclaimer, the term of this patent is extended or adjusted under 35 U.S.C. 154(b) by 145 days.

(21) Appl. No.: 15/254,281

(22) Filed: Sep. 1, 2016

(65) Prior Publication Data

US 2018/0055615 A1 Mar. 1, 2018

(51) Int. Cl.
*A61C 13/30* (2006.01)
*A61C 8/00* (2006.01)

(52) U.S. Cl.
CPC .......... *A61C 13/30* (2013.01); *A61C 8/0022* (2013.01); *A61C 8/0089* (2013.01)

(58) Field of Classification Search
CPC ..... A61C 13/30; A61C 1/185; A61B 17/8888; B25B 23/14; B25B 23/16; B25B 23/141; B25B 23/142; B25B 23/1415; B25B 23/1427; B25G 1/00; B25G 1/005; B25G 1/105
USPC ....... 433/103, 105, 107, 114, 117, 122, 141, 433/221; 81/467, 60, 177.4, 472–474, 81/490; 464/11, 68.1, 69
See application file for complete search history.

(56) References Cited

U.S. PATENT DOCUMENTS

| | | | | |
|---|---|---|---|---|
| 480,439 | A | * 8/1892 | Seaton | F16D 3/66 464/66.1 |
| 3,620,044 | A | * 11/1971 | Latour | F16F 15/10 464/74 |
| 4,239,489 | A | 12/1980 | Ellman et al. | |

(Continued)

FOREIGN PATENT DOCUMENTS

| EP | 0 305 934 A1 | 3/1989 |
|---|---|---|
| EP | 0 536 386 B1 | 6/1996 |
| WO | WO 2015/118543 A1 | 8/2015 |
| WO | WO 2015/132323 A1 | 9/2015 |

OTHER PUBLICATIONS

Cylindro-conical dental implant / titanium / tapered / self-drilling, Idall Implants Diffusion International, http://www.medicalexpo.com/prod/implants-diffusion-international/product-72776-660347.html, Feb. 1, 2016, 5 pages.

(Continued)

*Primary Examiner* — Matthew Saunders
(74) *Attorney, Agent, or Firm* — Oblon, McClelland, Maier & Neustadt, L.L.P.

(57) ABSTRACT

A damping dental post key configured to implant a dental root post for restoration of a tooth is described. The dental post key includes a body for handling and a post carrier having a key shape with respect to a head portion of the dental root post. During implantation of the dental post, rotation of the body compresses a set of springs in contact with the post carrier reducing a reaction force to a tooth root. In this way a limited force will be applied and a root fracture can be prevented. Further, the dental post key can be configured to have a fixed movement in a counterclockwise direction to remove the dental post and a free quarter-cycle movement with effort in a clockwise direction.

3 Claims, 16 Drawing Sheets

(56) References Cited

U.S. PATENT DOCUMENTS

| | | | |
|---|---|---|---|
| 4,344,306 A * | 8/1982 | Citron | F16D 7/10 464/34 |
| 4,479,783 A | 10/1984 | Weissman | |
| 4,480,997 A * | 11/1984 | Deutsch | A61C 13/30 433/221 |
| 4,490,116 A * | 12/1984 | Deutsch | A61C 13/30 433/215 |
| 4,738,616 A | 4/1988 | Reynaud | |
| 4,759,714 A | 7/1988 | Szegvary | |
| 4,778,388 A | 10/1988 | Yuda et al. | |
| 5,158,458 A * | 10/1992 | Perry | A61C 8/0089 433/141 |
| 5,545,089 A * | 8/1996 | Kirschey | F16D 3/68 464/160 |
| 5,775,910 A | 7/1998 | Orrico | |
| 6,131,477 A * | 10/2000 | Gaydek | F16D 3/68 464/74 |
| 6,439,086 B1 * | 8/2002 | Bahr | B25B 23/141 81/467 |
| 6,733,393 B2 * | 5/2004 | Rivin | F16D 3/66 464/66.1 |
| 8,051,751 B2 * | 11/2011 | Huang | B25B 23/1427 81/467 |
| 8,057,229 B2 | 11/2011 | Engström et al. | |
| 8,714,977 B2 | 5/2014 | Fromovich et al. | |
| 9,125,710 B2 | 9/2015 | Bassett et al. | |
| 9,163,713 B2 * | 10/2015 | Yoon | F16H 55/36 |
| 9,310,008 B2 * | 4/2016 | Beemer | B01L 3/563 |
| 9,572,617 B1 * | 2/2017 | Prado | A61B 17/8888 |
| 2002/0120275 A1 * | 8/2002 | Schmieding | A61B 17/8615 606/104 |
| 2007/0274800 A1 * | 11/2007 | Mikkonen | A61B 17/862 411/15 |
| 2009/0194307 A1 * | 8/2009 | Rinner | B25B 23/1427 173/181 |
| 2010/0275743 A1 * | 11/2010 | Wengreen | A61B 17/861 81/467 |
| 2010/0275745 A1 * | 11/2010 | Wengreen | A61B 17/8875 81/477 |
| 2010/0275746 A1 * | 11/2010 | Wengreen | A61B 17/8875 81/477 |
| 2014/0193775 A1 | 7/2014 | Hogan et al. | |
| 2016/0081774 A1 * | 3/2016 | Fah | A61C 8/0089 433/141 |
| 2016/0153519 A1 * | 6/2016 | Yoon | F16F 15/123 474/94 |

OTHER PUBLICATIONS

Goodacre CJ, et al., The prosthodontic management of endodontically treated teeth: a literature review. Part I. Success and failure data, treatment concepts, J Prosthodont., vol. 3, No. 4, Dec. 1994, pp. 243-250 (Abstract only).

C. González-Lluch, et al., "Influence of material and diameter of pre-fabricated posts on maxillary central incisors restored with crown", Journal of Oral Rehabilitation, vol. 36, Issue 10, Oct. 2009m pp. 737-747 (Abstract only).

Richard S. Schwartz, et al., "Post Placement and Restoration of Endodontically Treated Teeth: A Literature Review", Journal of Endodontics, vol. 30, No. 5, May 2004, pp. 289-301.

Carla Santina de Miranda Coelho, et al., "Finite element analysis of weakened roots restored with composite resin and posts", Dental Materials Journal, vol. 28, No. 6, Nov. 2009, pp. 671-678.

Xiao-na Li, et al., "Three-dimensional finite element analysis of a maxillary central incisor restored with different post-core materials", Int Chin J Dent, vol. 8, 2008, pp. 21-27.

Alessandro Lanza, et al., "3D FEA of cemented steel, glass and carbon posts in a maxillary incisor", Dental Materials, vol. 21, No. 8, Aug. 2005, pp. 709-715.

Dejak B, et al., "Finite element analysis of strength and adhesion of cast posts compared to glass fiber-reinforced composite resin posts in anterior teeth", J Prosthet Dent., vol. 105, No. 2, Feb. 2011, pp. 115-126 (Abstract only).

Dejak B, et al., "The influence of ferrule effect and length of cast and FRC posts on the stresses in anterior teeth", Dent Mater., vol. 29, No. 9, Sep. 2013, pp. 227-237 (Abstract only).

Durmus G, et al., "Effects of post core materials on stress distribution in the restoration of mandibular second premolars: a finite element analysis", J Prosthet Dent., vol. 112, No. 3, Sep. 2014, pp. 547-554 (Abstract only).

Genovese K, et al., "Finite element analysis of a new customized composite post system for endodontically treated teeth", J Biomech., vol. 38, No. 12, Dec. 2005, pp. 2375-2389 (Abstract only).

Morris HF, "Veterans Administration Cooperative Studies Project No. 147/242. Part VII: The mechanical properties of metal ceramic alloys as cast and after simulated porcelain firing", The Journal of Prosthetic Dentistry, vol. 61, No. 2, 1989, pp. 160-169 (Abstract only).

H. Sano, et al., "Tensile Properties of Mineralized and Demineralized Human and Bovine Dentin", Journal of Dental Research, vol. 73, No. 6, Jun. 1994, pp. 1205-1211.

Ronald L. Sakaguchi, et al., "Craig's Restorative Dental Materials, 13$^{th}$ Edition", 2006, pp. 61,65 and 391 (Abstract only).

* cited by examiner

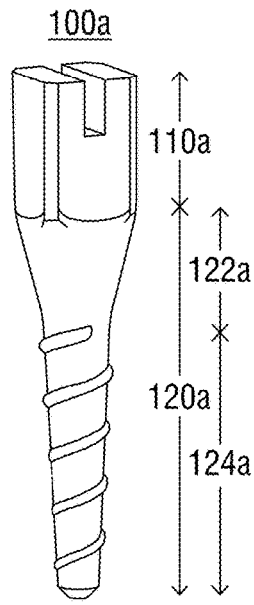 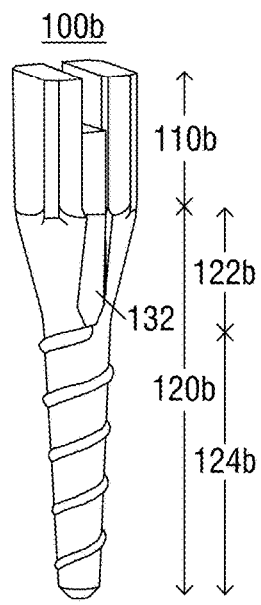 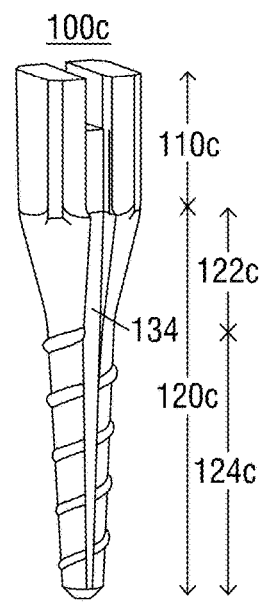
FIG. 1A  FIG. 1B  FIG. 1C
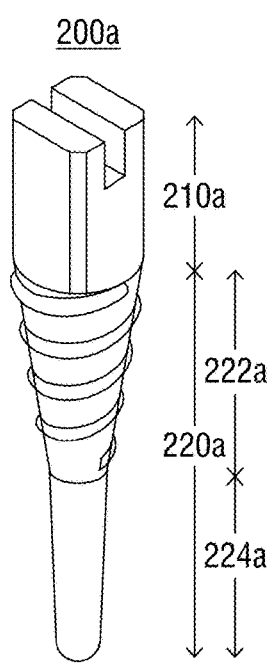 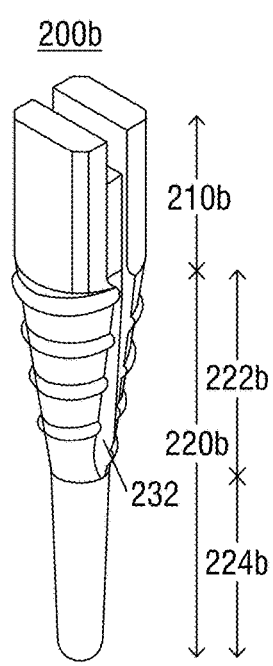 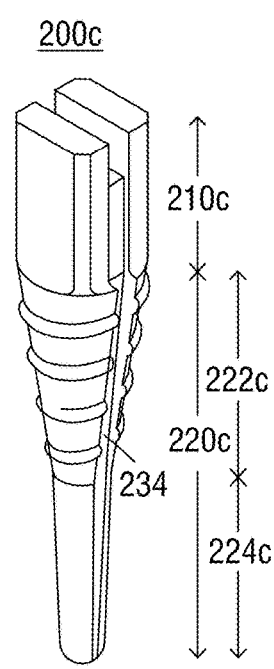
FIG. 2A  FIG. 2B  FIG. 2C

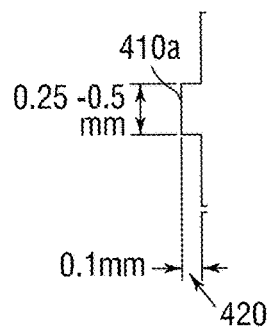 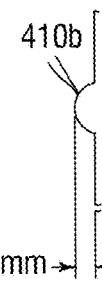 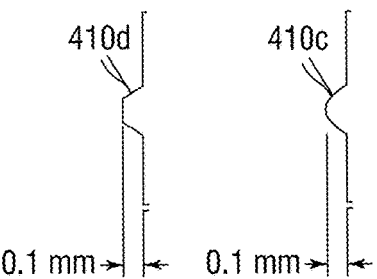
FIG. 4A  FIG. 4C  FIG. 4E
FIG. 4B  FIG. 4D
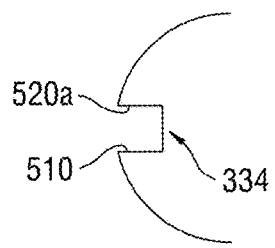 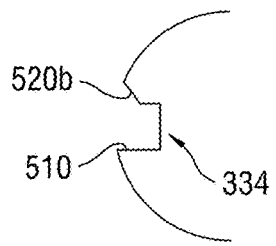 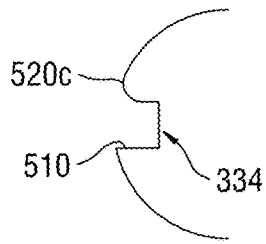
FIG. 5A  FIG. 5B  FIG. 5C
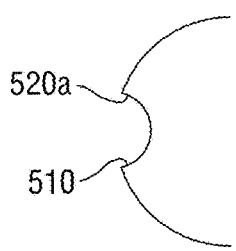 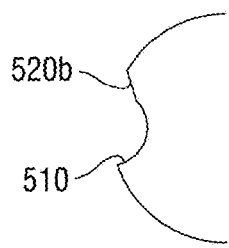 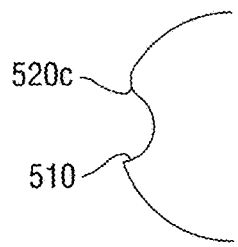
FIG. 5D  FIG. 5E  FIG. 5F
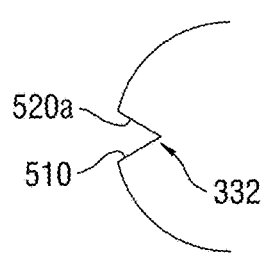 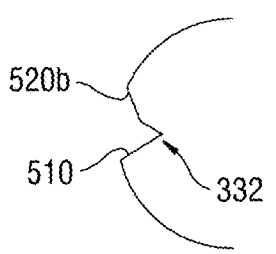 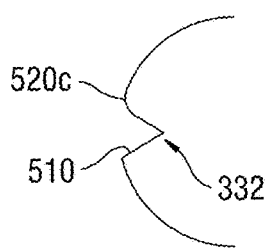
FIG. 5G  FIG. 5H  FIG. 5I

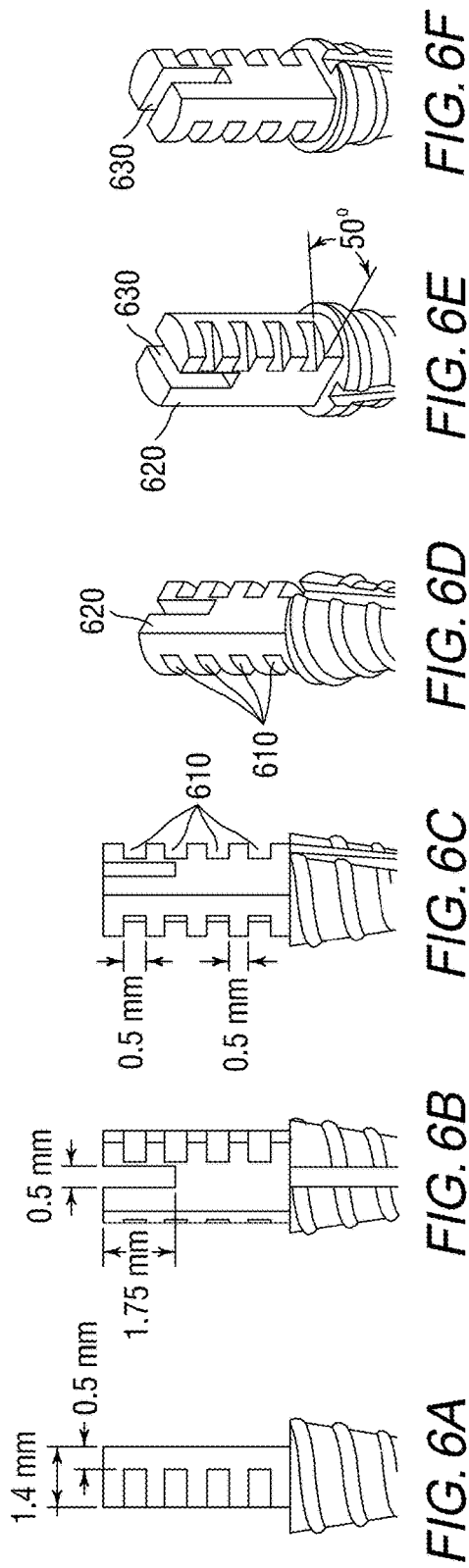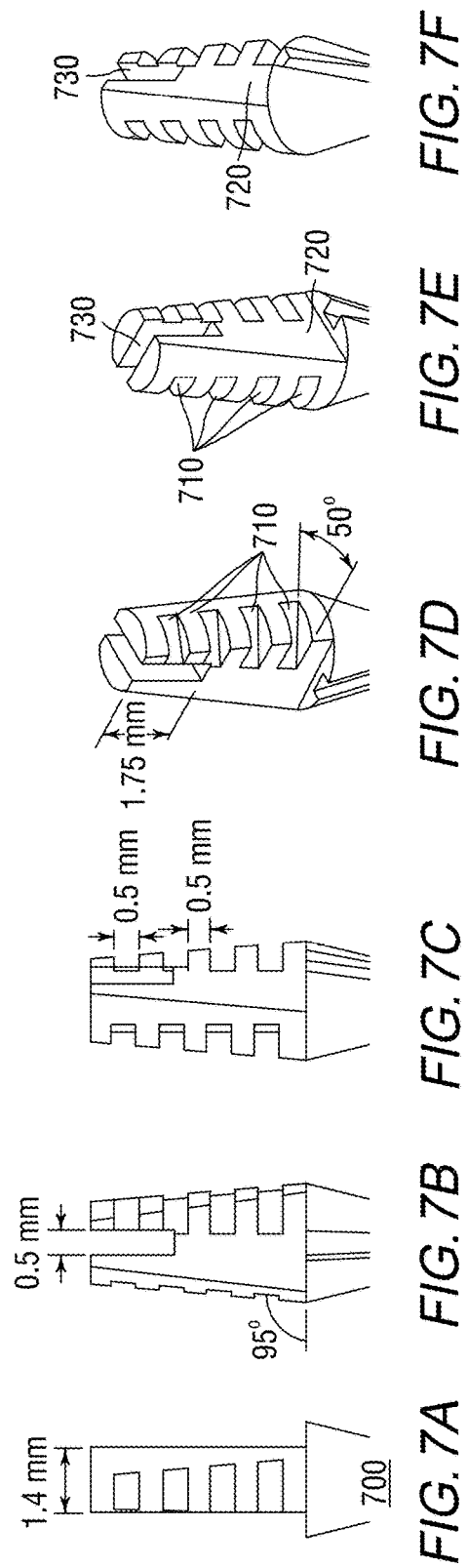

900a
(310a)

900a
(310a)

900a
(310a)

900a
(310a)

900b
(310a)

900b
(310a)

900b
(310a)

900b
(310a)

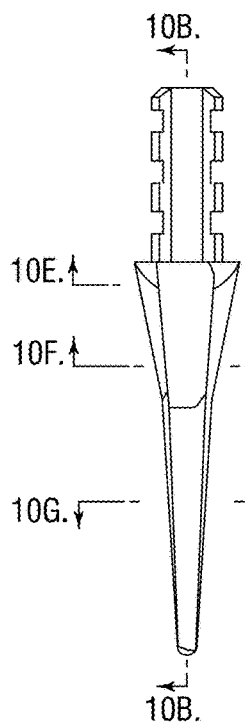
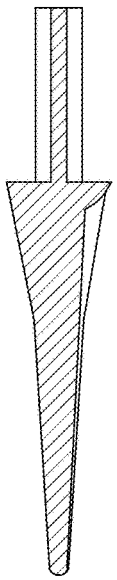
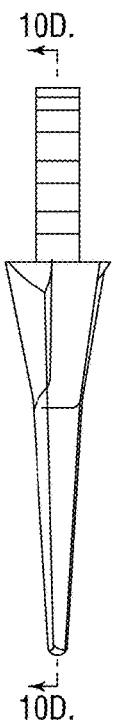
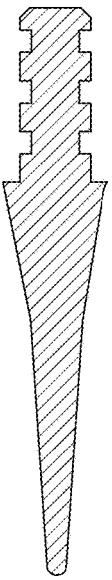
FIG. 10A  FIG. 10B  FIG. 10C  FIG. 10D
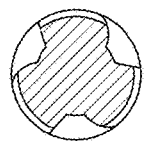
FIG. 10E
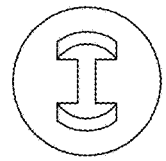
TOP VIEW
FIG. 10H
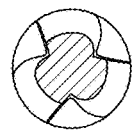
FIG. 10F
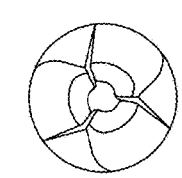
BOTTOM VIEW
FIG. 10I
FIG. 10G
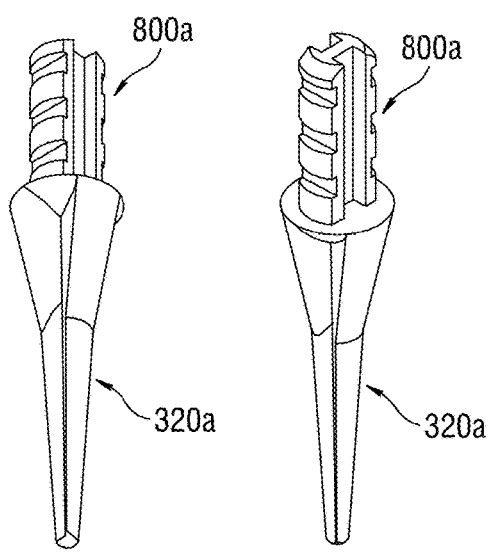
FIG. 10J  FIG. 10K

TOP VIEW

BOTTOM VIEW

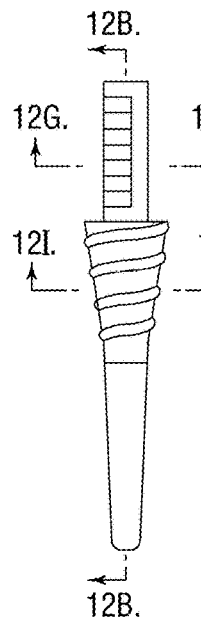
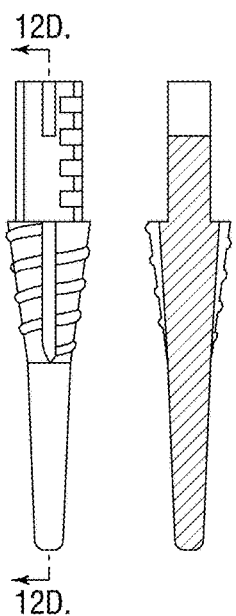
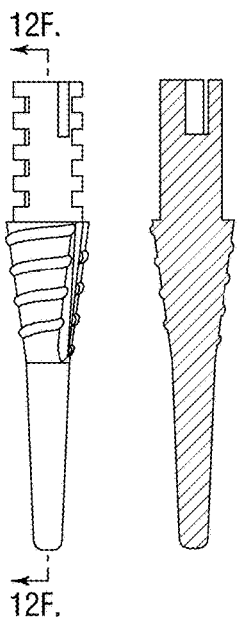
FIG. 12A  FIG. 12C  FIG. 12E
FIG. 12B  FIG. 12D  FIG. 12F
FIG. 12G
FIG. 12I
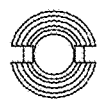
BOTTOM VIEW
FIG. 12J
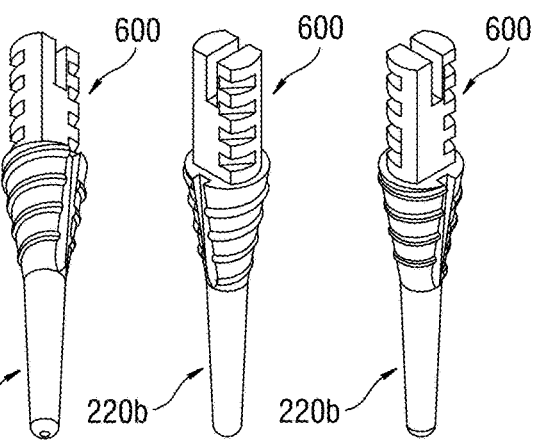
FIG. 12L
TOP VIEW
FIG. 12H
FIG. 12K  FIG. 12M FIG. 13A
FIG. 13C
FIG. 13E
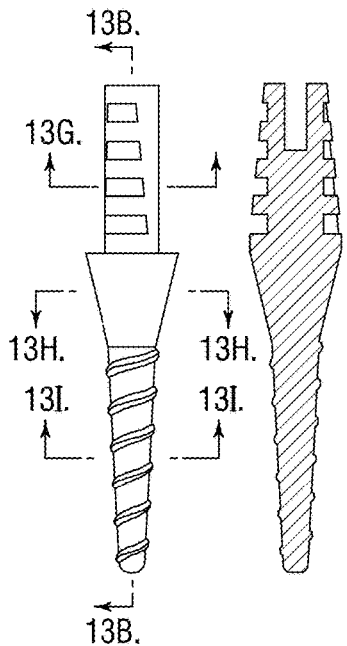
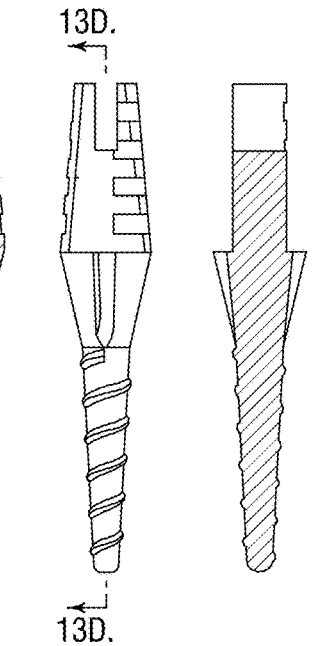
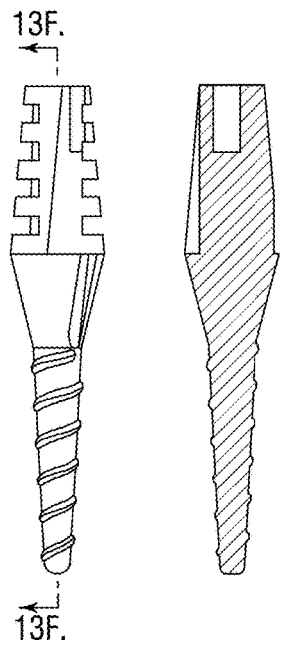
FIG. 13B
FIG. 13D
FIG. 13F
FIG. 13G
TOP VIEW
FIG. 13J
FIG. 13M
FIG. 13H
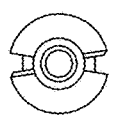
BOTTOM VIEW
FIG. 13K
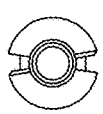
FIG. 13I
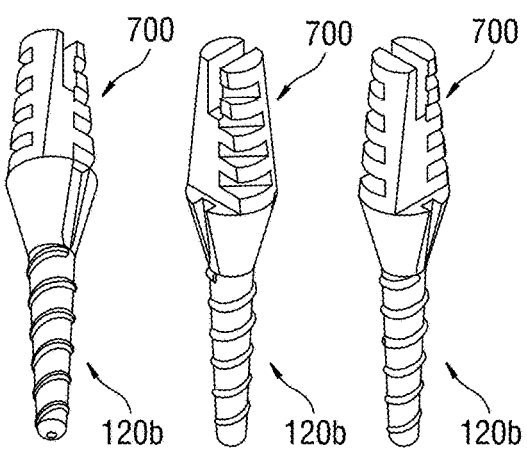
FIG. 13L          FIG. 13N

DAMPING DENTAL ROOT POST KEY

BACKGROUND

Field

The present disclosure relates to a damping dental post key for implanting a dental root post during restoration of a tooth.

SUMMARY

The present disclosure relates to a damping dental post key configured to implant a dental root post or dental post for restoration of a tooth. The dental post key includes a body for handling and a post carrier having a key shape with respect to a head portion of the dental post. During implantation of the dental post, rotation of the body compresses a set of springs in contact with the post carrier reducing a reaction force. This dynamic force configured to rotate the dental root post into a prepared root canal of the tooth in a smooth way. In this way a limited force will be applied and a root fracture can be prevented. Further, the dental post key can be configured to have a fixed movement in a counter-clockwise direction to remove the dental post and a free quarter-cycle movement with effort in a clockwise direction.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein:

FIG. 1A is a perspective view drawing of a dental post that is divided into a head portion and a root portion, where the root portion includes an apical section including threads and a cervical section without threads according to an example;

FIG. 1B is a perspective view drawing of the dental post of FIG. 1A including grooves that extend to only the cervical section of the root portion according to an example;

FIG. 1C is a perspective view drawing of the dental post of FIG. 1A including grooves that extend to the entire root portion according to an example;

FIG. 2A is a perspective view drawing of a dental post that is divided into a head portion and a root portion, where the root portion includes an apical section without threads and a cervical section including threads according to an example;

FIG. 2B is a perspective view drawing of the dental post of FIG. 2A including grooves that extend to only the cervical section of the root portion according to an example;

FIG. 2C is a perspective view drawing of the dental post of FIG. 2A including grooves that extend to the entire root portion according to an example;

FIGS. 4A-4E are a set of examples of an extrusion profile forming a thread in a longitudinal axis;

FIGS. 5A-5I are drawings of a set of examples of a horizontal cross-section shape of a groove;

FIGS. 6A-6F show different perspective views of a head portion having a set of horizontal grooves, a pair of flat surfaces, and a slot configured to receive a dental post key according to an example;

FIGS. 7A-7F show different perspective views of the head portion of FIGS. 6A-6F having tapered shape along longitudinal axis according to an example;

FIGS. 10A-10K show different side, perspective, and cross-sectional views a dental post including the head portion of FIGS. 8A-8D and the root portion of FIG. 3A according to an example;

FIGS. 12A-12M show different side, perspective, and cross-sectional views a dental post including the head portion of FIGS. 6A-6F and the root portion of FIG. 2B according to an example;

FIGS. 13A-13N show different side, perspective, and cross-sectional views a dental post including the head portion of FIGS. 7A-7F and the root portion of FIG. 1B according to an example;

DETAILED DESCRIPTION

Figure 3A:
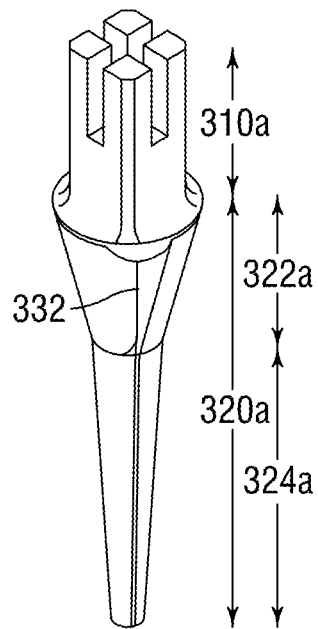
FIG. 3A is a perspective view drawing of a dental post that is divided into a head portion and a root portion, where the root portion includes a set of grooves, where each groove has a V-shape according to an example.

The present disclosure relates to a dental root post for restoration of a tooth, and a damping dental post key for implanting a threaded dental post into a prepared root canal. The dental post is configured to give enhanced retention to a tooth core as well as for final restoration materials and end caps. The dental post can be divided into a head portion and a root portion, each having different features depending on a depth required for the restoration. The root portion is configured to have two conical level sections; a cervical flared shape section and apical conical section to obtain more adaptation to the root canal. The head portion can be configured to serve for reconstruction a core with a composite material or an amalgam or any permanent dental filling material. The dental post is preferably made from a metal such as stainless steel and titanium or an alloy such as Ni—Cr alloy, but can be any other suitable material. A root channel can be initially prepared by use of suitable instruments having a same shape and wider size (0.2 mm) of the root post. The dental root post can subsequently be implanted and secured to the tooth with dental cement.

Referring now to the drawings, wherein like reference numerals designate identical or corresponding parts throughout the several views.

Dental Post Model 1

In a first embodiment, a dental post 100a-c can be divided into a head portion 110a-c and a root portion 120a-c. The root portion 120a-c includes a cervical section 122a-c having a flared shape and an apical section 124a-c having threads (See FIGS. 1A, 1B, 1C). The flared shape has a thickness such that mastication stress will be configured to concentrate on an upper or coronal part of the cervical section 122a-c. The apical section 124a-c is configured to give stabilization and allow conservation of a root tissue. The cervical section 122a-c is configured to give maximum support to a final restoration by transferring stress to the coronal part of the root tissue and to provide more protection from harmful stress on the apical root tissue.

The cervical section 122a-c is non-active (i.e. non-threaded) and flare shaped radially-decreasing conical axial profile along longitudinal axis between for example 6-18 degrees. The apical section 124a-c is active (i.e. threaded) tapered radially-decreasing conical axial profile along longitudinal axis between for example 1-5 degrees.

The dental post 100a-c is preferably used for roots having short-length and can have no grooves or 1 to 2 grooves. The grooves allow excessive cement to flow outside a tooth root canal and prevent from hydraulic pressure between the dental root post and the tooth's canal wall. The grooves can have different shapes as shown in FIGS. 5A-5I. The threads of the apical section 124a-c can be configured to serve as an anchor and can have different shapes with for example 0.1 mm height and for example 0.25 to 0.5 mm width, as shown in FIGS. 4A-4E.

FIG. 1A shows an example of a dental post 100a without groves. FIG. 1B shows an example of a dental post 100b including grooves 132 that extend to only the cervical section 122b of the root portion 120b. The grooves can extend to the entire root portion or only to the cervical section depending on the post sizes (i.e. length and diameter). In an example, the grooves can extend 0.5 to 1 mm diameter on cervical level. In an example, the grooves can extend 0.2 to 0.5 mm on the apex level. FIG. 1C shows an example of a dental post 100c including grooves 134 that extend to the entire root portion 120c.

Dental Post Model 2

In a second embodiment, a dental post 200a-c can be divided into a head portion 210a-c and a root portion 220a-c that includes a cervical section 222a-c having a flared shape and threads, and an apical section 224a-c (See FIGS. 2A, 2B, 2C).

The cervical section 222a-c is active (i.e. threaded) and flare-shaped radially-decreasing conical axial profile along longitudinal axis between for example 6-18 degrees. The apical section 224a-c is non-active (i.e. non-threaded) tapered radially-decreasing conical axial profile along longitudinal axis between for example 1-5 degrees.

The dental post 200a-c can have no grooves or 1 to 4 grooves. The grooves can extend to the entire root portion or only to the cervical section, with 0.5 to 1 mm diameter on cervical level and 0.2 to 0.5 mm on the apex level, depending on the post sizes (i.e. length and diameter). The grooves allow excessive cement to flow outside the tooth root canal and prevent from hydraulic pressure. The grooves can have different shapes as shown in FIGS. 5A-5I. The threads of the cervical section 222a-c can be configured to serve as an anchor and can have different shapes with for example 0.1 mm height and for example 0.25 to 0.5 mm width, as shown in FIGS. 4A-4E.

FIG. 2A is an example of a dental post 200a without groves. FIG. 2B is an example of a dental post 200b including grooves 232 that extend to only the cervical section 222b of the root portion 220b. FIG. 2C is an example of a dental post 200c including grooves 234 that extend to the entire root portion 220c.

Dental Post Model 3

Figure 3B:
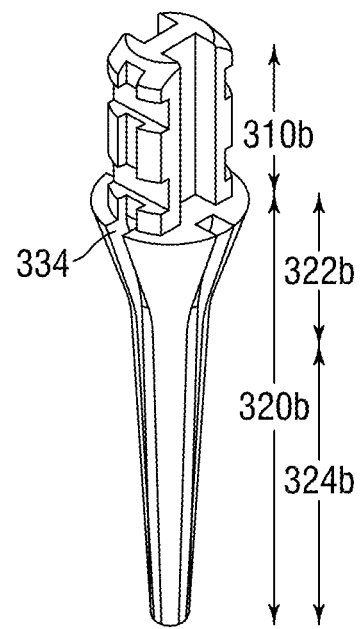
FIG. 3B is a perspective view drawing of a dental post that is divided into a head portion and a root portion, where the root portion includes a set of grooves, where each groove has a square-shape according to an example.
Figure 8A:
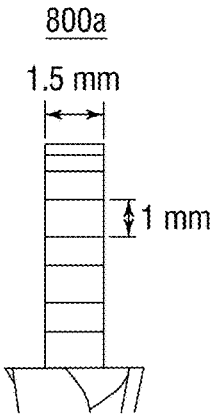
FIGS. 8A-8D show different side, perspective, and cross-sectional views of a head portion having a set of horizontal grooves, a pair of flat surfaces, and a slot configured to receive a dental post key according to an example.
Figure 8B:
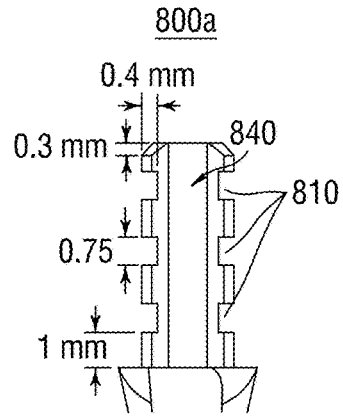
Figure 8C:
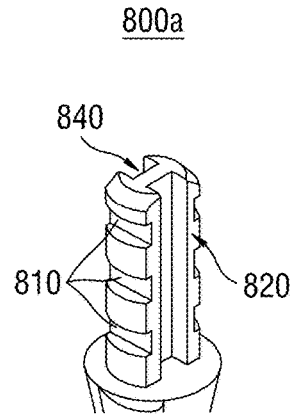
Figure 8D:
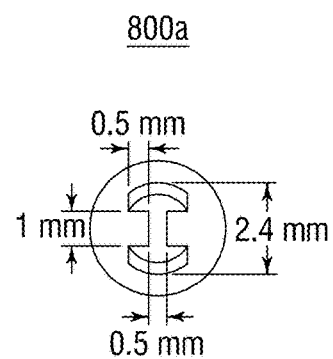
Figure 8E:
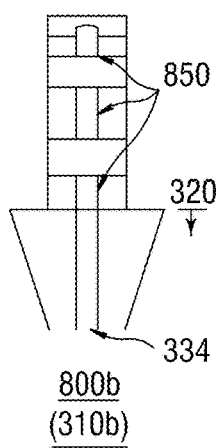
FIGS. 8E-8H show a cross-sectional and perspective view of the head portion shown in FIGS. 8A-8D further including a second set of vertical grooves along longitudinal axis that intersect the set of horizontal grooves according to an example.
Figure 8F:
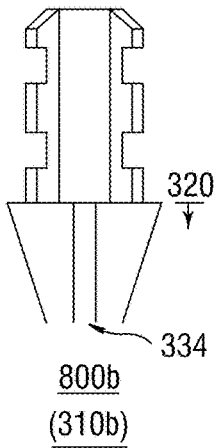
Figure 8G:
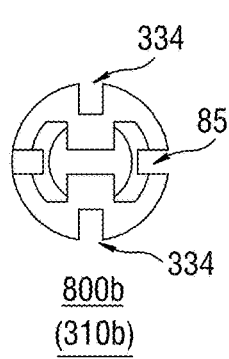
Figure 8H:
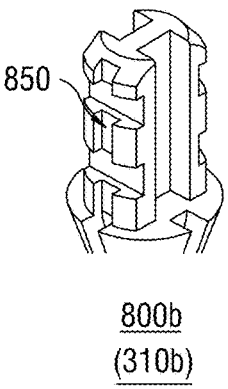
Figure 9A:
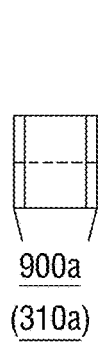
FIGS. 9A-9D show different side, perspective, and cross-sectional views of a head portion having a square shape and a slot configured to receive a dental post key according to an example.
Figure 9B:
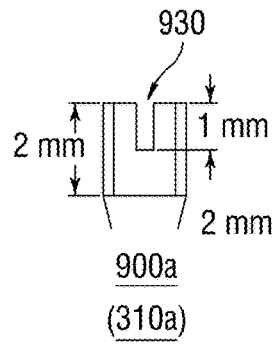
Figure 9C:
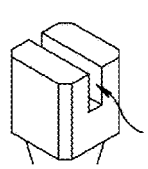
Figure 9D:
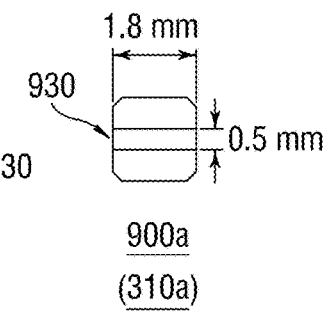
Figure 9E:
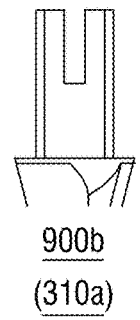
FIGS. 9E-9H show a cross-sectional and perspective view of the head portion shown in FIGS. 9A-9D further including a second slot that intersects the first slot according to an example.
Figure 9F:
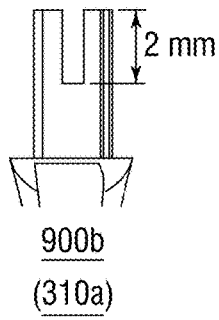
Figure 9G:
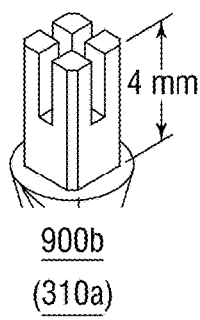
Figure 9H:
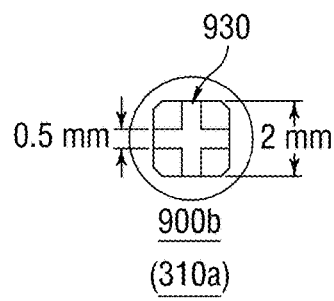
Figures 11A, 11B, 11C, 11D:
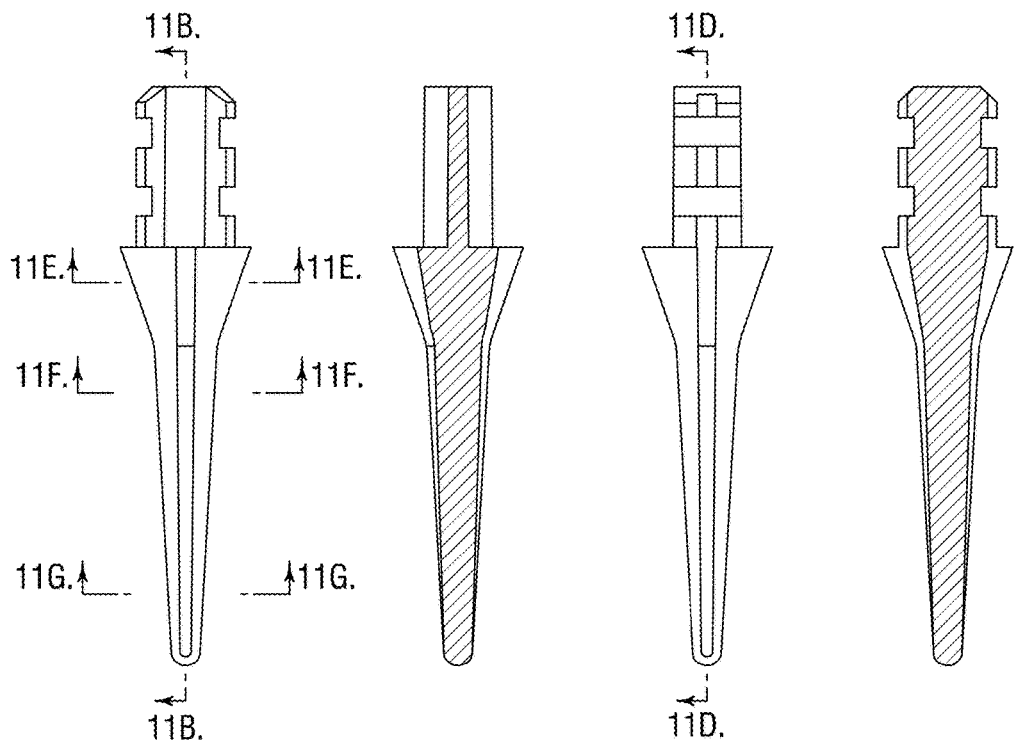
FIGS. 11A-11K show different side, perspective, and cross-sectional views a dental post including the head portion of FIGS. 8E-8H and the root portion of FIG. 3B according to an example.
Figure 11E:
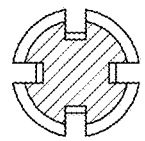
Figure 11H:
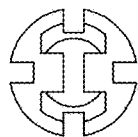
Figure 11F:
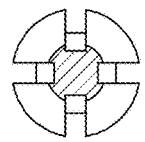
Figure 11I:
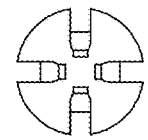
Figure 11G:
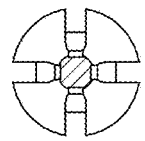
Figure 11J:
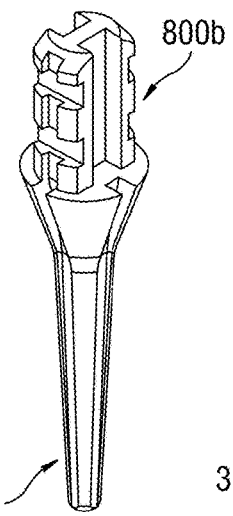
Figure 11K:
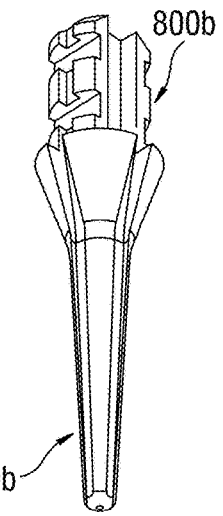

In a third embodiment, a dental post 300a-b includes a head portion 310a-b and a root portion 320a-b which includes a cervical section 322a-b and an apical section 324a-b (See FIGS. 3A, 3B). FIG. 3A is an example of a dental post 300a including a head portion 310a (See FIGS. 9E-9H) and a root portion 320a having three grooves, where each groove has a V-shape 332 (See FIGS. 5G-5I). FIG. 3B is an example of a dental post 300b including a head portion 310b (See FIGS. 8E-8H) and a root portion 320b having four grooves, where each groove has a square-shape 334 (See FIGS. 5A-5C). The cervical section 322a-b is non-threaded and has a flared-shape having a radially-decreasing conical axial profile along a longitudinal axis between for example 6-18 degrees. The apical section 324a-b is non-threaded tapered radially-decreasing conical axial profile along a longitudinal axis between for example 1-5 degrees. The dental post 300a-b can have no grooves or 1 to 4 grooves that extend to the entire root portion 320a-b.

The grooves can have a diameter and a depth which radially-decrease along a longitudinal axis of the dental post 300. The grooves can have different shapes as shown in FIGS. 5A-5I. Each groove can have a cutting active edge 510 in the clockwise direction and a non-active edge 520b-c in the counterclockwise direction. The cutting active edge 510 enables the dental post 300a-b to be inserted and placed into a root channel without using excessive force. Also during insertion of the dental post 300a-b, the cutting active edge 510 can be configured to allow soft self-drilling into the tooth root to give more retention and stabilization to the dental post 300a-b.

Threads & Grooves

FIGS. 4A-4E show different examples of a cross-section of an extrusion profile 410a-e forming a thread. Each extrusion profile 410a-e can have an extrusion length 420. In an example, the extrusion length 420 can be 0.1 mm, but can also be any suitable length.

FIGS. 5A-5I show horizontal cross-sections of examples of the grooves. In an aspect, the groves can have a square shape (See FIGS. 5A, 5B, 5C), a curve shape (See FIGS. 5D, 5E, 5F), and a V-shape (See FIGS. 5G, 5H, 5I). In an aspect, the active edge 510 and non-active edge 520b-c of the groves can have a beveled edge 520b (See FIGS. 5B, 5E, 5H), or a fillet edge 520c (See FIGS. 5C, 5F, 5I).

Head Portion Model 1

FIGS. 6A-6F show perspective views of examples of a head portion 600 having a set of horizontal grooves 610, a pair of flat surfaces 620, and a slot 630 configured to receive a dental post key. The head portion 600 can have a body with for example a circular cylindrical shape. FIGS. 7A-7F show perspective views of examples of a head portion 700 having a set of horizontal grooves 710, a pair of flat surfaces 720, and a slot 730 configured to receive a dental post key. The head portion 700 can have a body with circular tapered shape (e.g. 5 degree taper). Both the head portion 600 and the head portion 700 can have two flat surfaces 620, 720 along longitudinal axis, and a slot 630, 730 (e.g. 0.4 to 0.6 mm width and 1 to 2 mm height) configured to receive a respective dental post key for driving purposes. In horizontal direction, the head portion can include 2 to 8 grooves 610, 710 depending on a height of the head portion, and a 50 degree angle between the flat surface 620, 720 and the grooves 610, 710. In an enxample, the grooves 610, 710 can have a diameter of 0.5 to 0.75 mm. A total height of the head portion can vary between for example 2.5 to 6 mm.

Head Portion Model 2

In a third example, FIGS. 8A-8H show perspective views of examples of a head portion 800a-b having a body with a circular cylindrical shape, a set of horizontal grooves 810, a pair of flat surfaces 820 along longitudinal axis, and a first set of vertical grooves 840 along longitudinal axis. Optionally, the head portion 800b can have a second set of vertical grooves 850 (See FIGS. 8E-8H). The optional additional vertical grooves 850 can have a groove diameter (e.g. 0.5 mm) based on a head size and a head diameter. In an example, the first set of vertical grooves 840 along longitudinal axis can have a 1 mm diameter. In an example, the set of horizontal grooves 810 can include 2 to 8 corresponding grooves 810, each with a 0.5 to 0.75 mm diameter, based on a height of the head portion 800. The height of the head portion 800a-b can vary between 3 to 7 mm.

Head Portion Model 3

FIGS. 9A-9H show side and perspective views of examples of a head portion 900a-b. The head portion 900a-b can include a horizontal section having a square shape and either one slot 930 (See FIGS. 9A-9D) or two slots 930 (See FIGS. 9E-9H) for inserting a respective key for driving purposes. The horizontal section can have a width of 1.8 to 2.5 mm and a height of 2 to 4 mm. Each slot 930 can have a width of 0.4 to 0.6 mm and a height of 1-2 mm according to an example.

Figure 19A:
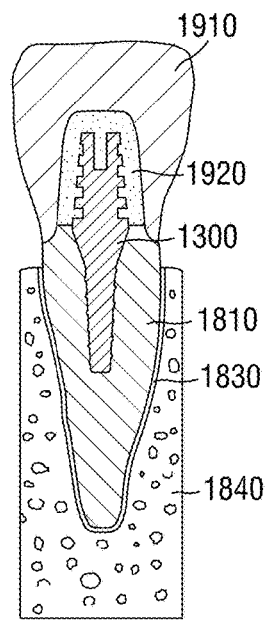
FIG. 19A shows a cross-section view of an example of a tooth model having a root surrounded by periodontal ligament and bone, and restored with the dental post of FIG. 13B, core and crown according to an example.
Figure 19B:
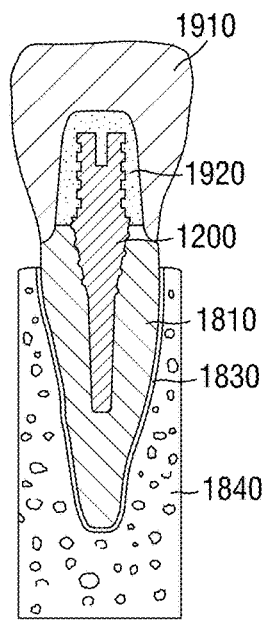
FIG. 19B shows a cross-section view of a tooth model of FIG. 19A restored with the dental post of FIG. 12B, core and crown according to an example.
Figure 19C:
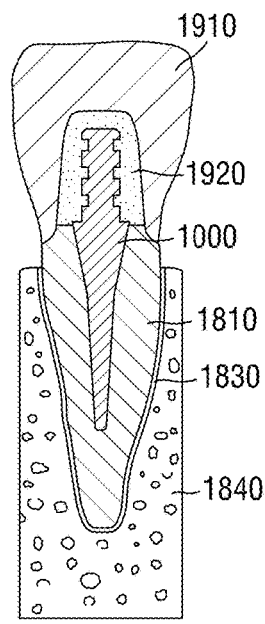
FIG. 19C shows a cross-section view of a tooth model of FIG. 19A restored with the dental post of FIG. 10D, core and crown according to an example.

FIGS. 10A-10K are of cross-sectional and perspective views of an example of a dental post including the head portion 800a (FIGS. 8A-8D) and the root portion 320a (FIG. 3A). FIGS. 11A-11K are of cross-sectional and perspective views of an example of the dental post 300b, which includes the head portion 800b (FIGS. 8E-8H) and the root portion 320b (FIG. 3B). FIGS. 12A-12M are of cross-sectional and perspective views of an example of a dental post including the head portion 600 (FIGS. 6A-6F) and the root portion 220b (FIG. 2B). FIGS. 13A-13N are of cross-sectional and perspective views of an example of a dental post including the head portion 700 (FIGS. 7A-7F) and the root portion 120b (FIG. 1B). Obviously, different combinations of the different head portions and the different root portions are possible and are within the spirit and the scope of the present embodiments. FIGS. 19A-19C show cross-sectional views of an example of a tooth model having a tooth root 1810 surrounded by a periodontal ligament 1830 and a bone 1840. The tooth model is shown restored with different root posts 1300, 1200, 1000 (See FIGS. 13B, 12B, 10D), core 1920 and crown 1910.

Dental Post Key

During implantation of a dental post, a dental post key can be used to create a smooth reaction force to implant a threaded dental post into the tooth root. In this way a limited force will be applied and a root fracture can be prevented. Further, the dental post key can be configured to have a fixed movement in a counterclockwise direction to remove the dental post and a free quarter-cycle movement with effort in a clockwise direction.

Figure 14A:
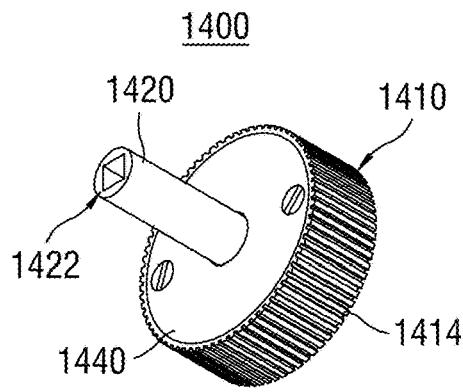
FIG. 14A shows a perspective drawing of a dental post key including a body having a cover and a post carrier, protruding the cover, having a key shape configured to turn a respective dental post according to an example.

FIG. 14A shows a perspective drawing of a dental post key 1400 including a body 1410 for handling and a post carrier 1420 having a distal end with a key shape 1422 configured to turn a respective dental post. The dental post key 1400 is shown with a cover 1440 for the body 1410 with a central opening configured to allow a portion of the post carrier 1420 to pass through. The body 1410 can have a plurality of ridges 1414 on an outer surface configured to enhance gripping by an operator. A proximal end of the post carrier has an elongated shape. The body includes a pair of abutments 1412 configured to prevent the post carrier from rotating. Each abutment 1412 can include a threaded hole 1444 configured to receive a screw, such that the cover 1440 can be secured by a set of screws 1442 to each abutment 1412 according to an example.

Figure 14B:
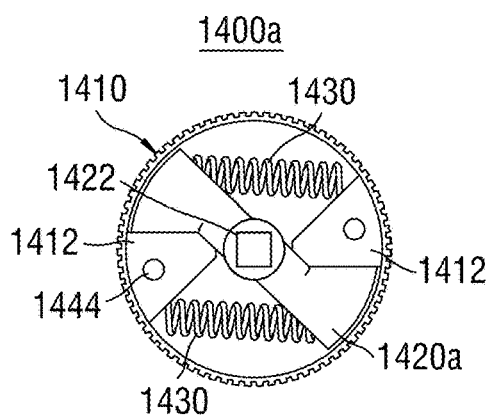
FIG. 14B shows a drawing of a dental post key, without the cover, including a set of springs configured to resist a force between the post carrier and the body according to an example.
Figure 14C:
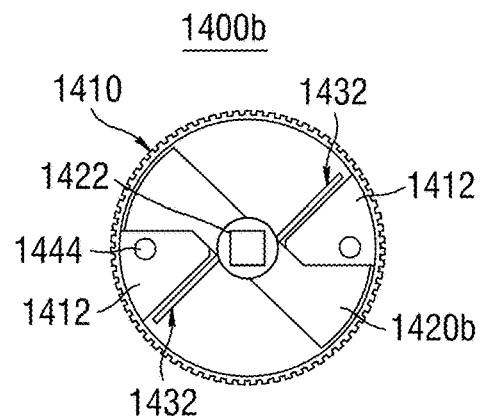
FIG. 14C shows a drawing of a dental post key, without the cover, including a set of torsion springs configured to resist a force between the post carrier and the body according to an example.
Figure 14D:
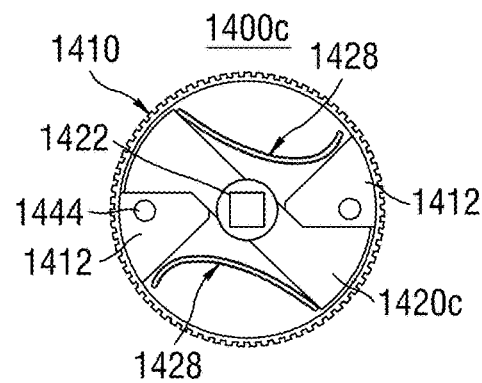
FIG. 14D shows a drawing of a dental post key, without the cover, including a post carrier having a set of plate spring configured to resist a force between the post carrier and the body according to an example.
Figure 14E:
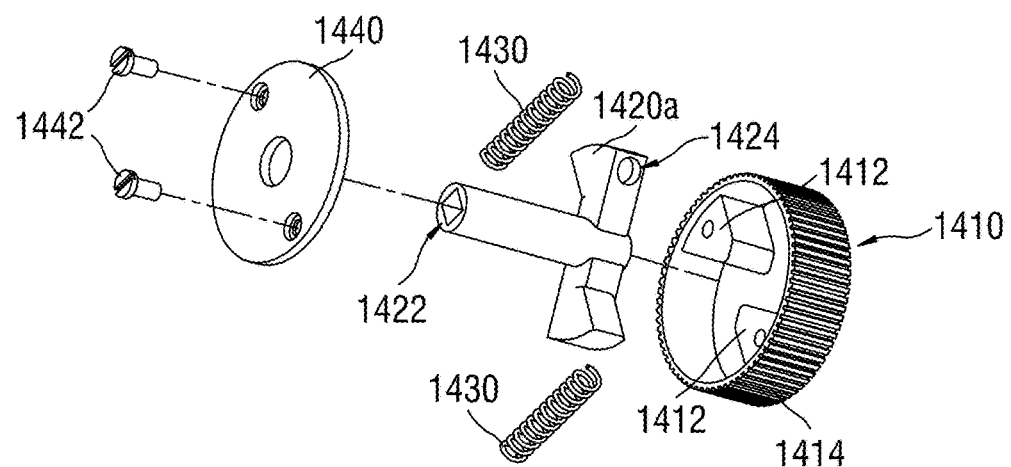
FIG. 14E shows a perspective drawing of expanded parts of the dental post key of FIG. 14B with cover according to an example.

In an example, a dental post key 1400a can include a set of springs 1430 that are configured to connect, or resist a force between, a post carrier 1420a to the body 1410 (See FIGS. 14B, 14E). Alternatively, the dental post key 1400a can include only one spring 1430 configured to connect the post carrier 1420a to the body 1410. In an example, each spring can be configured to have a different spring constant. In an example, a dental post key can include a first spring having a first spring constant and a second spring having a second spring constant. In an example, the second spring constant is substantially different than the first spring constant such that, when the dental post key is rotated, each spring is configured to create a dynamic reaction force to implant the dental root post into the tooth root.

FIG. 14E shows a perspective drawing of expanded parts of the dental post key of FIG. 14B according to an example. The post carrier 1420a and the two abutments 1412 having a set of securing areas (e.g. holes) 1424 configured to secure the set of springs 1430. FIGS. 15A-15F show a series of perspective views of an example of the post carrier 1420a.

Figure 14F:
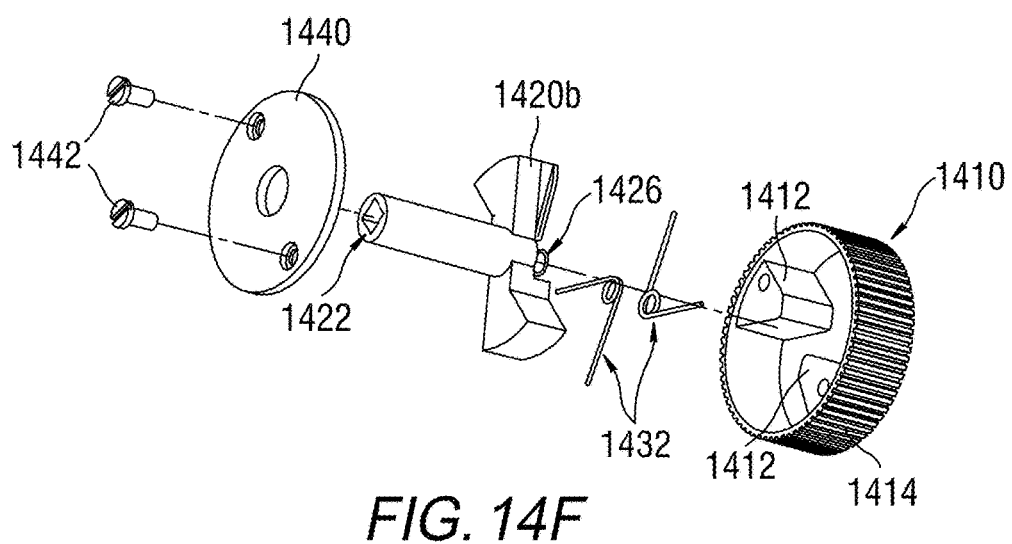
FIG. 14F shows a perspective drawing of expanded parts of the dental post key of FIG. 14C with cover according to an example.
Figure 15A:
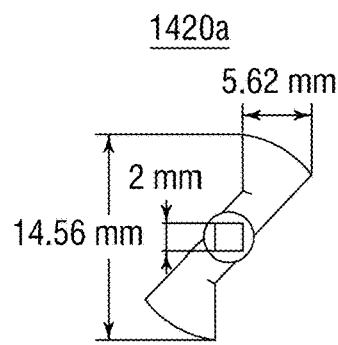
FIGS. 15A-15F show a series of perspective views of the post carrier of FIG. 14B according to an example.
Figure 15B:
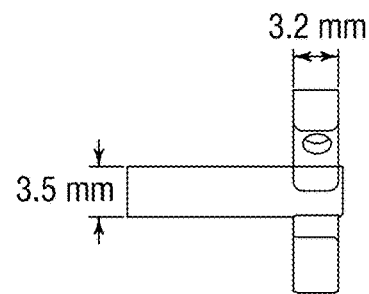
Figure 15C:
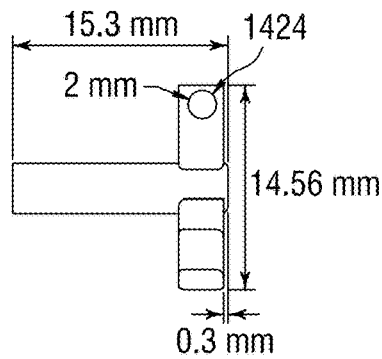
Figure 15D:
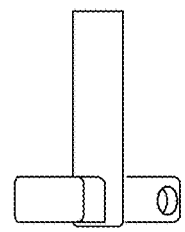
Figure 15E:
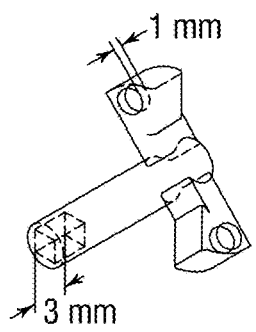
Figure 15F:
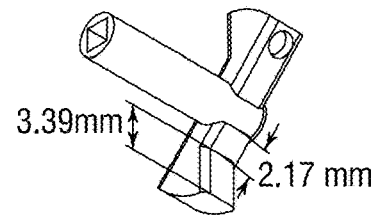
Figure 16A:
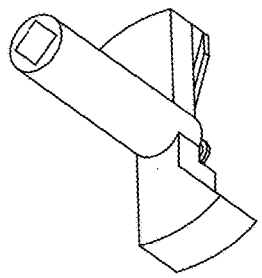
FIGS. 16A-16G are a series of perspective views of the post carrier of FIG. 14C according to an example.
Figure 16B:
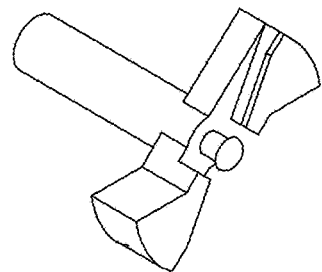
Figure 16C:
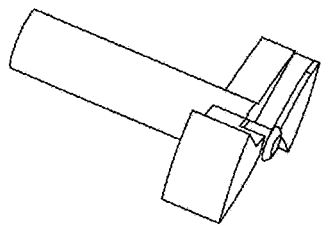
Figure 16D:
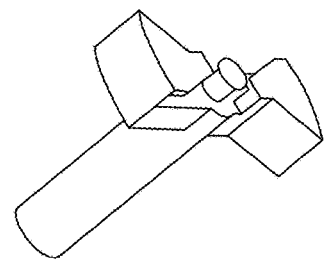
Figure 16E:
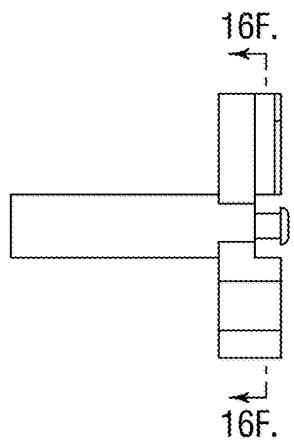
Figure 16F:
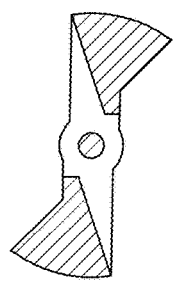
Figure 16G:
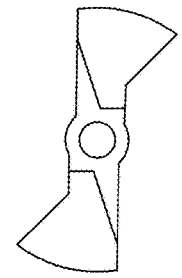
Figure 17A:
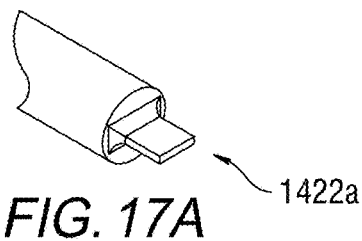
FIGS. 17A-17F are a series of perspective views of examples of the key shape of a post carrier configured to match a respective dental post.
Figure 17B:
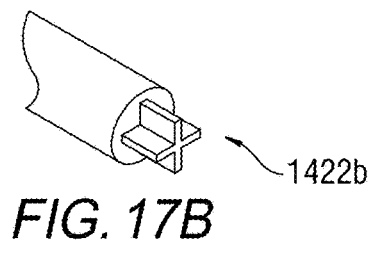
Figure 17C:
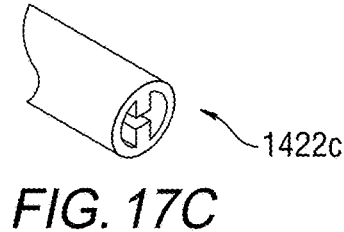
Figure 17D:
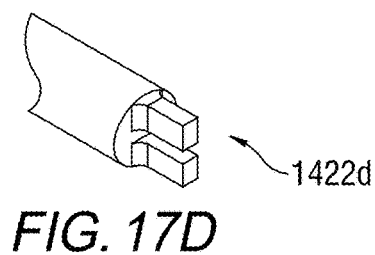
Figure 17E:
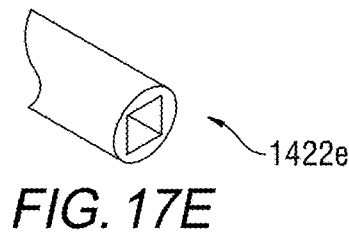
Figure 17F:
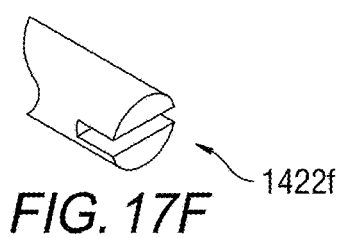

In an example, a dental post key 1400b can include a set of torsion springs 1432 that are configured to connect, or resist a force between, a post carrier 1420b to the body 1410 (See FIGS. 14C, 14F). FIG. 14F shows a perspective drawing of expanded parts of the dental post key of FIG. 14C according to an example. The post carrier 1420b is shown having a knob 1426 configured to secure the set of torsion springs 1432. The knob 1426 can be recessed into the proximal end of the post carrier 1420b.

In an example, a dental post key 1400c can include a post carrier 1420c having at least one plate spring 1428 that is configured to connect, or resist a force between, the post carrier 1420c to the body 1410 (See FIG. 14D). In an example, the plate spring 1428 can be an extension of a shape of the post carrier 1420c. In another example, the spring 1428 can be a separate piece.

FIGS. 16A-16G are a series of perspective views of an example of the post carrier 1420b. FIGS. 17A-17F are a series of perspective views of examples of a key shape of a post carrier configured to match a respective dental post.

Figure 18:
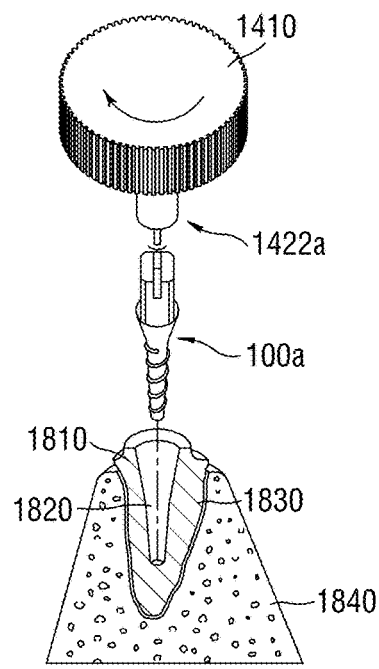
FIG. 18 shows an example of a dental post key and a dental post of FIG. 1A that will implant into a prepared root canal of a tooth model in a clockwise direction according to an example.

FIG. 18 shows an example of a dental post key with the post carrier 1422a (see FIG. 17A), and the post model 100a (see FIG. 1A) that is configured to be implanted into a prepared root canal 1820 of a tooth root 1810 in clockwise direction. The cross-sectional view of the tooth model shows the tooth root 1810 surrounded by the periodontal ligament 1830 and the bone 1840.

Obviously, numerous modifications and variations of the present invention are possible in light of the above teachings. It is therefore to be understood that within the scope of the appended claims, the invention may be practiced otherwise than as specifically described herein.

The invention claimed is:

1. A dental post key to implant a dental root post in a tooth root, the dental post key comprising: a body having an exterior surface and an abutment on an inner surface; and a post carrier having a distal end configured to have an opening having a shape configured to receive the dental root post, a proximal end having a rigid elongated shape that is configured to be in contact with a first side of the abutment of the body, a flexible elongated shape that is configured to be in contact with a second side of the abutment of the body, the post carrier further having a second flexible elongated shape, wherein the flexible elongated shape is configured to have a first spring constant and the second flexible shape is configured to have a second spring constant that is different than the first spring constant, wherein, when the body is rotated, a combination of both flexible elongated shapes is configured to create a dynamic reaction force to implant the dental root post into the tooth root.

2. The dental post key of claim 1, the body having a second abutment, wherein the rigid elongated shape of the post carrier is configured to be in contact with the first side of the abutment of the body, wherein the flexible elongated shape of the post carrier is configured to be in contact with the second abutment of the body.

3. A method for implanting a dental root post, the method comprising:
   matching a post carrier to a shape of the dental root post;
   assembling a dental post key using the post carrier; and
   rotating a body of the dental post key,
   wherein a spring and a second spring are located between the post carrier and the body of the dental post key,
   wherein, during the rotating, the post carrier is in direct contact with the dental root post, and the dental root post is in direct contact with a tooth root,
   wherein the spring is configured to have a first spring constant, and the second spring is configured to have a second spring constant that is different than the first spring constant, and
   wherein, during the rotating, each spring is configured to create a dynamic reaction force between the dental root post and the tooth root.

* * * * *

UNITED STATES PATENT AND TRADEMARK OFFICE
CERTIFICATE OF CORRECTION

PATENT NO. : 10,245,128 B2
APPLICATION NO. : 15/254281
DATED : April 2, 2019
INVENTOR(S) : Bassam Nawaf Srayeddin It is certified that error appears in the above-identified patent and that said Letters Patent is hereby corrected as shown below:

On the Title Page

Item (73), the Assignees' information is missing. Item (73) should read:
-- (73) Assignees: National Guard Health Affairs, Riyadh (SA); King Saud bin Abdulaziz University for Health Sciences, Riyadh (SA); King Abdullah International Medical Research Center, Riyadh (SA) --

Signed and Sealed this
Third Day of September, 2019

Andrei Iancu
*Director of the United States Patent and Trademark Office*